United States Patent
Bille

(10) Patent No.: US 8,403,484 B2
(45) Date of Patent: Mar. 26, 2013

(54) LASER CONTROL WITH PHASE PLATE FEEDBACK

(75) Inventor: Josef F. Bille, Heidelberg (DE)

(73) Assignee: Heidelberg Engineering GmbH (DE)

( * ) Notice: Subject to any disclaimer, the term of this patent is extended or adjusted under 35 U.S.C. 154(b) by 89 days.

(21) Appl. No.: 13/111,664

(22) Filed: May 19, 2011

(65) Prior Publication Data

US 2011/0216314 A1 Sep. 8, 2011

Related U.S. Application Data

(62) Division of application No. 12/259,924, filed on Oct. 28, 2008, now Pat. No. 7,988,295.

(51) Int. Cl.
*A61B 3/10* (2006.01)

(52) U.S. Cl. ........................................ 351/221

(58) Field of Classification Search ................ 351/221, 351/246, 205, 206, 211, 213
See application file for complete search history.

(56) References Cited

U.S. PATENT DOCUMENTS

| | | | |
|---|---|---|---|
| 6,095,651 A | 8/2000 | Williams et al. | |
| 7,270,413 B2 * | 9/2007 | Hirohara et al. | 351/246 |
| 7,270,415 B2 * | 9/2007 | Yamaguchi et al. | 351/221 |
| 2003/0143391 A1 | 7/2003 | Lai | |
| 2006/0274408 A1 * | 12/2006 | Lauer | 359/386 |
| 2007/0258046 A1 | 11/2007 | Lai | |

OTHER PUBLICATIONS

Bille, Josef F., et al., "Compact adaptive optics system for multiphoton fundus imaging", Journal of Modern Optics, Feb. 20-Mar. 10, 2008, pp. 749-758, vol. 55, Nos. 4-5, Taylor & Francis, London, England.

* cited by examiner

*Primary Examiner* — Hung Dang
(74) *Attorney, Agent, or Firm* — Nydegger & Associates

(57) ABSTRACT

An ophthalmic imaging system includes a light source, focusing optics, compensating optics, and a computer that coordinates both of the optics to optimize the Diffraction Limited Point Spread Function (DL-PSF) of the imaging light beam. In detail, the compensating optics includes a customized phase plate that provides substantially complete compensation for static aberrations introduced by an eye into the imaging light beam. Further, the computer measures an operational error signal that results from dynamic aberrations. The computer then uses the error signal to control the compensating optics and thereby optimize the DL-PSF by compensating for both static and dynamic aberrations. For an alternate embodiment, an active mirror can be included in the compensating optics to provide additional compensation for the dynamic aberrations.

8 Claims, 1 Drawing Sheet

LASER CONTROL WITH PHASE PLATE FEEDBACK

This application is a divisional of application Ser. No. 12/259,924, filed Oct. 28, 2008, now U.S. Pat. No. 7,988,295, the entire contents of which is incorporated herein by reference.

FIELD OF THE INVENTION

The present invention pertains generally to ophthalmic imaging systems. More particularly, the present invention pertains to systems and methods for altering an imaging light beam to compensate for both static and dynamic aberrations that are introduced into the beam by an eye; and to thereby optimize the Diffraction Limited-Point Spread Function (DL-PSF) of the light beam. The present invention is particularly, but not exclusively, useful for systems and methods having a custom phase plate that provides for perfect static compensation and, in combination with computer-controlled feedback, provides compensation for dynamic aberrations introduced into an imaging light beam.

BACKGROUND OF THE INVENTION

For ophthalmic imaging systems that involve scanning microscopy, the detail and resolution of the resultant image is directly dependent on both the size of the illuminating light beam's focal spot, and the quality of the optics in the imaging system. As for the size of the focal spot, particularly when imaging an eye's retinal tissue, it is desirable that the spot size be as small as possible. Due to the structural size of retinal tissues, this means that spot sizes of around only two microns in diameter may be useful. As for the quality of the optical system, this factor is typically evaluated by what is known as the Point Spread Function (PSF). More specifically, the PSF pertains to an intensity distribution that describes the response of an imaging system to a point source of light or to a point object. The degree of spreading (i.e. blurring) of the point object is then a measure for the quality of the imaging system.

Not surprisingly, the PSF of an imaging system can be adversely affected by several factors. In particular, image resolution with a PSF will be limited by such factors as imperfections in the lenses of the optical system, a misalignment of the lenses and, in the specific case of ophthalmic imaging applications, aberrations introduced by the eye itself. On this last point, it is to be appreciated that when imaging the retina, the anterior components of the eye (i.e. the cornea and the lens of the eye), as well as the retina need to be considered along with the optical components of the imaging system. Due to diffraction, however, there is still a fundamental maximum to the resolution that can be attained by an imaging system. Specifically, an optical (imaging) system having the ability to produce images with an angular resolution that is as good as the instrument's theoretical limit is said to be "diffraction limited." Thus, for ophthalmic imaging systems, the objective is to attain a Diffraction Limited Point Spread Function (DL-PSF).

A technical concept associated with the PSF of an imaging system that operates close to its diffraction limit is the "Strehl Ratio." By definition, the Strehl Ratio is the ratio of an observed peak intensity compared with the theoretical maximum peak intensity of a perfect imaging system working at the diffraction limit. Stated differently, the Strehl Ratio can be defined as the best focus of the imaging system. Importantly, the Strehl Ratio for a given optical (imaging) system is determinable, and variations therefrom are observable.

In the context of an ophthalmic imaging system, it is known that when anatomically introduced optical aberrations are introduced into the light beam of an optical system they can be measured. Further, it is known that such aberrations can be compensated for. For example, U.S. patent application Ser. No. 12/204,674 for an invention entitled "Custom Phase Plate," which is assigned to the same assignee as the present invention, discloses a customized phase plate for removing optical aberrations from a light beam when they have been introduced by the retina and the anterior components of an eye. Optical aberrations that are anatomically introduced, however, are both static and dynamic. This is in contrast with an optical (imaging) system that remains substantially static during an imaging procedure.

In light of the above, it is an object of the present invention to provide a system and method to compensate for static and dynamic aberrations that are introduced into an imaging light beam during an imaging procedure. Another object of the present invention is to provide and maintain a substantially DL-PSF for a high quality optical system during an imaging procedure. Still another object of the present invention is to provide a system and method for optimizing the PSF of an imaging system that is easy to use, is relatively simple to manufacture and is comparatively cost effective.

SUMMARY OF THE INVENTION

In accordance with the present invention, an optical (imaging) system for maintaining a Diffraction Limited Point Spread Function (DL-PSF) during imaging of the retina of an eye uses a custom phase plate to remove anatomically-introduced optical aberrations from an imaging light beam. In addition to removing static aberrations that may be introduced by the eye during an imaging procedure, the system also includes computer-generated feedback to remove dynamic aberrations from the imaging light beam. In one embodiment of the present invention, the computer-generated feedback is used to control rotation of the custom phase plate, in concert with linear movement of a focus/defocus unit, to compensate for dynamically introduced optical aberrations. In an alternate embodiment, an active mirror is controlled by a computer for this same purpose. In both embodiments, the custom phase plate provides essentially perfect static compensation for optical aberrations introduced by a specific eye.

Structurally, the system of the present invention includes a laser unit for generating a laser beam. When generated, the laser beam is directed onto a beam path toward the retinal tissue in the eye that is to be imaged. A focus/defocus unit (i.e. a lens) is positioned on the path to establish a focal spot on the tissue that is to be imaged. Importantly, this focal spot has an observable Point Spread Function (PSF). Additionally, a custom phase plate is positioned on the beam path to compensate for static optical aberrations that are introduced into the laser beam by the eye being imaged.

As intended for the present invention, the custom phase plate is specifically created for the eye being imaged. In detail, the phase plate has a substantially flat surface with a plurality of contiguous spots formed thereon. Importantly, each spot on this surface establishes a specified Optical Path Difference (OPD) for light passing through that spot on the phase plate. Collectively, the plurality of spots creates a diffraction pattern that is determined by wavefront analysis to compensate for the static aberrations introduced by the eye.

Along with the custom phase plate, the system includes a computer that essentially evaluates the system's Strehl Ratio to create an error signal. In accordance with standard feedback control theory, the error signal provides feedback for optimizing the DL-PSF of the system. As indicated above, in one embodiment of the system, this error signal is used to coordinate movements of the focus/defocus unit (translation) and the custom phase plate (rotation). For an alternate embodiment, the error signal provides input to an active mirror. In both instances, control is provided in the system to compensate for dynamic and spherical aberrations that are introduced into the optical (imaging) system during an imaging procedure.

Operationally, the present invention can be described in terms of wavefront formation. In this perspective, the laser unit initially generates a light beam having a substantially plane wavefront. This light beam is then directed toward the retina of an eye, and is focused to a focal spot on the retinal tissue to be imaged. As indicated above, this focal spot has an observable PSF. However, as the light beam passes through the custom phase plate, en route to the retina, the plane wavefront that is generated by the laser unit is altered by the custom phase plate to create a compensated wavefront. It is this compensated wavefront that will pass through the anterior components (i.e. cornea and lens) of the eye. The light that is reflected from the retina and out of the eye will then have a reflected wavefront. It is this reflected wavefront that is compared with the plane wavefront to obtain the error signal. The computer is then used to minimize the error signal in the compensated wavefront for improvement of the PSF (i.e. optimization of the DL-PSF).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
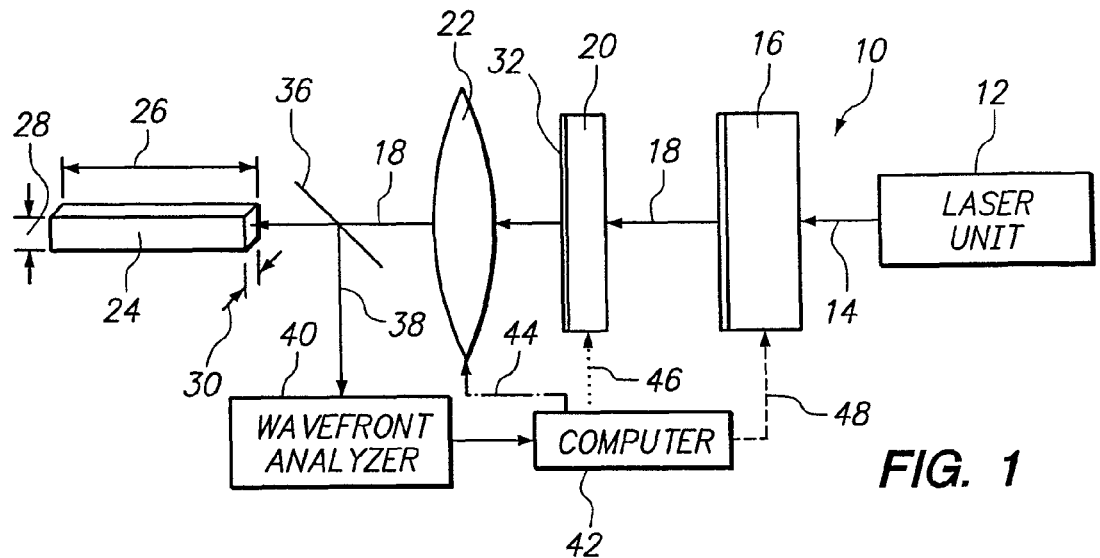
FIG. 1 is a schematic representation of a system in accordance with the present invention.

Referring initially to FIG. 1, an optical (imaging) system in accordance with the present invention is shown and is generally designated 10. As shown, the system 10 includes a laser unit 12 for generating a laser beam 14 that is directed toward an active mirror (optional) 16 along a beam path 18. Preferably, the laser beam 14 will be a pulsed beam having pulses with durations in the femto-second range.

Still referring to FIG. 1 it is seen that the laser beam 14 passes through a custom phase plate 20 and through a lens 22 that focuses the laser beam 14 to a focal spot having a point spread function (PSF) 24. Typically, as envisioned by the present invention, the PSF 24 will have a length 26 that will be in a range between ten and twenty microns, a height 28 that will be approximately two microns, and a width 30 that will also be approximately two microns. For purposes of the system 10, the lens 22 will function as a focus/defocus unit that independently operates in cooperation with the phase plate 20, or with the active mirror 16. In this combination, the lens 22 functions as focusing optics, and the phase plate 20, with or without the active mirror 16, functions as compensating optics.

In detail, the phase plate 20 is customized for each individual patient (not shown). To do this, the phase plate 20 has a substantially flat surface 32 that is formed with a plurality of contiguous spots. Importantly, each spot on the surface 32 establishes a specified Optical Path Difference (OPD) for light in the laser beam 14 as it passes through that spot on the phase plate 20. Collectively, the plurality of spots creates a diffraction pattern that is based on a wavefront analysis of the patient's eye 34 (see FIG. 2). As intended for the present invention, the custom phase plate 20 is manufactured to provide for substantially perfect static compensation for optical aberrations introduced by the eye 34.

FIG. 1 also indicates that light reflected from a target being illuminated by the PSF 24, will be directed by a turning mirror 36 along a path 38 toward a wavefront analyzer 40. The output of the wavefront analyzer 40 is then fed to a computer 42. In FIG. 1 the dot-dash line 44 further shows that the computer 42 is electronically connected to the focus/defocus unit of lens 22. Similarly, the computer 42 is electronically connected to the custom phase plate 20 (indicated by dotted line 46), and to the active mirror 16, if used (indicated by dashed line 48). Together, these various connections comprise a feedback control system as generally illustrated in FIG. 2, wherein the input laser beam 14 is altered by a feedback 50 in response to a transfer function "G" for focus of the beam 14 to a PSF 24 in an eye 34.

Figure 2:
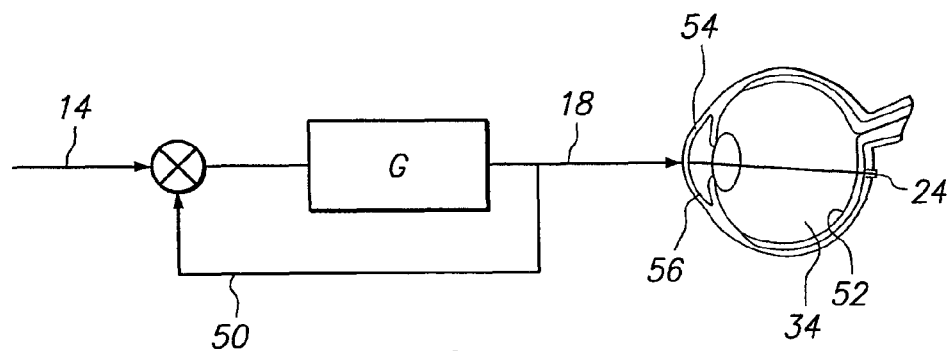
FIG. 2 is a simplified feedback control diagram for the system of the present invention shown in an operational relationship with an eye.

FIG. 2 also clearly illustrates the fact that when the laser beam 14 is focused to a focal spot with a PSF 24 on the retina 52 of an eye 34, light in the beam 14 passes through the anterior components of the eye 34. Specifically, the light will pass through both the cornea 54 and the lens 56 of the eye 34. As noted above, the anterior components of the eye 34 will introduce optical aberrations into the laser beam 14 that, if not compensated for, will have a deleterious effect on the desired DL-PSF of the system 10.

Figure 3:
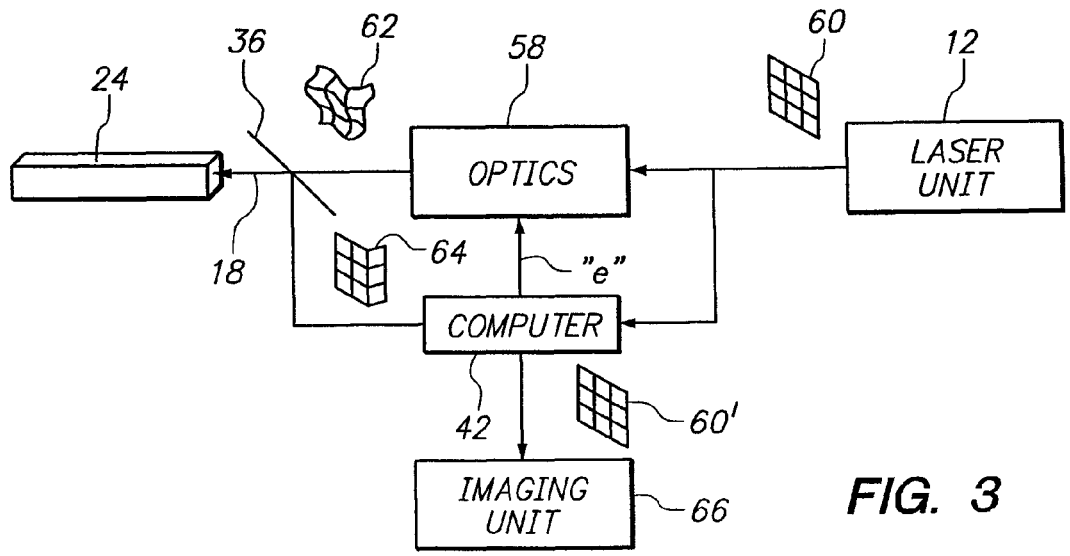
FIG. 3 is an illustration of various wavefronts created during an operation of the system of the present invention.

Operationally, the system 10 is perhaps best understood with reference to FIG. 3. There it is to be appreciated that the optics 58 essentially include the lens 22, the phase plate 20 and the active mirror 16 (if used), as shown in FIG. 1. Further, the operational aspects of the wavefront analyzer 40 (see FIG. 1) are included in the operation of the computer 42. With this in mind, FIG. 3 shows that the laser unit 12 initially generates the laser beam 14 with a plane wavefront 60. The optics 58 then alters the plane wavefront 60 to create a compensated wavefront 62. It is this compensated wavefront 62 that is created by the custom phase plate 20 to provide for essentially perfect static compensation for the optical aberrations that are introduced by the anterior components (i.e. cornea 54 and lens 56) and the retina 52 of the eye 34. It is also this compensated wavefront 62 that is directed toward the retina 52 of eye 34 for creation of the PSF 24.

Light of the PSF 24 that is reflected from the retina 52 will have a reflected wavefront 64 that results after the compensated wavefront 62 passes through the eye 34. The reflected wavefront 64 is then measured by the wavefront analyzer 40 and compared with the plane wavefront 60 by the computer 42 to create an error signal "e". Note: in the static case, the reflected wavefront 64 would be essentially the same as plane wavefront 60. In this case, the error signal "e" would be zero. The dynamic case, however, is different and the dynamic changes that are introduced by the eye 34 are manifest in the reflected wavefront 64. Thus, the error signal "e" essentially accounts for dynamic changes in optical aberrations that are introduced into the system 10. As envisioned by the present invention, the error signal "e" can be measured as a deviation from the Strehl Ratio of the system 10. If so, variations in the intensity of the reflected wavefront 64 from the theoretical maximum provided by a DL-PSF can be measured and used for the purpose of controlling the system 10.

For the purposes of the present invention, the error signal "e" can be effectively used for two different purposes. For one, it can be is used by the computer 42 for feedback control of the optics 58. Specifically, the error signal "e" can be used to rotate the phase plate 20 in conjunction with a translation of the lens 22 or, alternatively, it can be used to change configurations of the active mirror 16. In each of these instances, the error signal "e" will manipulate the optics 58 to maintain an optimal PSF 24. As another use of the error signal "e", FIG. 3 indicates it can be used to modify the reflected wavefront 64 to create a plane (imaging) wavefront 60' that can be used by an imaging unit 66 for viewing the target structure on which the PSF 24 has been focused. In the specific instance where the system 10 is used for scanning microscopy, the PSF 24 can be directed over a target (e.g. retina 52) and the sequence of resultant pixels can be arranged by the imaging unit 66 as required.

While the particular Laser Control With Phase Plate Feedback as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for optimizing a Diffraction Limited Point Spread Function (DL-PSF) for a laser beam having static and dynamic aberrations, the system comprising:
   a laser unit for generating the laser beam and for directing the laser beam onto a beam path;
   a focus/defocus unit positioned on the beam path to establish a focal spot having a Point Spread Function;
   a custom phase plate having a substantially flat surface with a plurality of spots formed thereon, wherein each spot has a specified Optical Path Difference (OPD), and the plurality of spots creates a diffraction pattern to compensate for aberrations in the laser beam to provide an optimized DL-PSF for the laser beam; and
   a computer means for coordinating a rotation of the phase plate with a movement of the focus/defocus unit to optimize the DL-PSF.

2. A system as recited in claim 1 wherein the custom phase plate effectively compensates for aberrations introduced into the laser beam characterized as astigmatism, coma and trefoil.

3. A system as recited in claim 2 wherein the custom phase plate removes substantially all static aberrations from the laser beam.

4. A system as recited in claim 3 further comprising an active mirror positioned on the beam path to provide a sequence of configurations of the active mirror for dynamic compensation of spherical aberrations and removal thereof from the laser beam.

5. A system as recited in claim 4 wherein the diffraction pattern of the custom phase plate, and the configurations of the active mirror are based on a wavefront analysis.

6. A system as recited in claim 4 further comprising a computer means for coordinating changes of the active mirror with movements of the focus/defocus unit to optimize the DL-PSF.

7. A system as recited in claim 1 wherein rotation of the phase plate is responsive to an error signal generated by deviations from a Strehl Ratio for the system.

8. A system as recited in claim 1 wherein the focus/defocus unit is a lens.

* * * * *